United States Patent [19]

Cognion et al.

[11] Patent Number: 4,620,050

[45] Date of Patent: Oct. 28, 1986

[54] PROCESS FOR THE MANUFACTURE OF ETHYLENE FROM ETHYL ESTERS

[75] Inventors: Jean-Marie Cognion, Saint Genis Laval; Pierre Durual, Vernaison, both of France

[73] Assignee: ATOCHEM, France

[21] Appl. No.: 771,981

[22] Filed: Sep. 3, 1985

[30] Foreign Application Priority Data

Sep. 17, 1984 [FR] France ................................ 84 14399

[51] Int. Cl.⁴ ............................................. L07C 1/253
[52] U.S. Cl. .................................. 585/640; 585/408; 585/469; 585/651
[58] Field of Search ............... 585/640, 639, 638, 408, 585/469, 733, 78 M, 651

[56] References Cited

U.S. PATENT DOCUMENTS

| | | | |
|---|---|---|---|
| 2,882,244 | 4/1959 | Milton | 423/328 |
| 3,130,007 | 4/1964 | Breck | 423/328 |
| 3,530,198 | 9/1970 | Fenton | 585/638 |
| 4,270,015 | 5/1981 | Knifton | 585/640 |
| 4,306,106 | 12/1981 | Kerr et al. | 585/639 |
| 4,399,305 | 8/1983 | Schreck | 562/607 |
| 4,554,397 | 11/1985 | Stern et al. | 585/638 |

OTHER PUBLICATIONS

Makens et al., J. Am. Chem. Soc., 61, 3203 (1939).
Senderens, Bull. Soc. Chem. France, 1908, 4, Nr. 3, 826.
John F. Knifton, Journal of Catalysis 79, 147–155 (1983).

*Primary Examiner*—Asok Pal
*Attorney, Agent, or Firm*—Sigalos & Levine

[57] ABSTRACT

Process for the manufacture of high purity ethylene by the decomposition in the gaseous phase of certain aliphatic carboxylic acid esters, at a temperature between about 150° and 300° C. in the presence of a zeolite having a pore diameter above about 0.6 nm as the catalyst.

7 Claims, No Drawings

PROCESS FOR THE MANUFACTURE OF ETHYLENE FROM ETHYL ESTERS

BACKGROUND OF THE INVENTION

The present invention concerns the production of ethylene by the catalytic decomposition of ethyl esters of carboxylic acids.

Ethylene is presently produced essentially by steam cracking of light petroleum fractions.

The depletion of petroleum and the increase of its cost are causing industry to seek to diversify the approaches to the manufacture of ethylene in order to satisfy economically the increasing demand for this product, particularly for ethylene of high purity quality.

The direct synthesis by a FISCHER TROPSCH reaction from the $CO/H_2$ mixture which is the synthesis gas prepared from coal or natural gas is unfortunately non-selective.

The dehydration of ethanol, a vegetable or sugar fermentation product, leads selectively to ethylene only but at a still prohibitive cost.

The catalytic condensation of methanol, particularly carefully studied on synthetic zeolites by MOBIL OIL CORPORATION and which uses raw material easily accessible from the synthesis gas did not permit reconciling selectivity and productivity.

Another approach to ethylene is the thermal decomposition, or pyrolysis, of ethyl esters. This pyrolysis has long been known and it takes place at temperatures which can reach 500° to 600° C.

For example, in J. Am. Chem. Soc. 61, 1939, 3203, R. F. MAKENS and W. G. EVERSOLE describe the pyrolysis of ethylene formate at a temperature of 375° C. or less. The ethylene formed is not only accompanied by decomposition products of formic acid, but also by a significant quantity of hydrocarbons such as methane, ethane, and butylene.

U.S. Pat. No. 4,270,015 describes obtaining ethylene esters by the catalytic reaction of an aliphatic carboxylic acid containing 2 to 4 carbon atoms with synthesis gas; other than that of ethylene and of the acid from which the ester derives, by pyrolysis of the latter in a quartz reactor at a temperature of the order of practically 450° C.

The ethylene produced contains other hydrocarbons, particularly ethane, as it is also reported by JOHN F. KNIFTON in Journal of Catalysis 79, 147–155 (1983).

The concentration of ethane can reach high values, near 5% by pyrolyzing pure ethyl propionate, at 460° C.

Furthermore, the conversion of the ester and the productivity in terms of ethylene are low.

In order to try to remedy the drawbacks of noncatalytic pyrolysis of ethyl esters, it has been proposed to use catalytic decomposition.

U.S. Pat. No. 4,399,305 describes obtaining high purity ethylene from ethyl acetate with the help of a catalyst composed of a perfluorosulfonic resin commercially sold under the trademark NAFION by duPONT de NEMOURS.

Although the gaseous portion of the product collected after pyrolysis is said to be high purity ethylene, the productivity of the process described remains low as a result of a conversion of the ester not surpassing 20% in the mode of embodiment of the invention which is, however, the best one. Furthermore, no mention is made of the selectivity.

Prior art also informs us that the use of catalysts based on alumina or on silica-alumina does not permit satisfying the present requirements of the industry.

For example, ethyl acetate leads to an ethylene strongly polluted by $CO_2$ when, according to SENDERENS, Bull. Soc. Chem. France, 1908, 4, NR.3, 826, it is decomposed at 300° C. on alumina and when, according to R. D. OBOLENTSEV and Yu. N. USOV, Doklady Akad. Nauk. SSSR, F1,1950,489, it is decomposed at 400° C. on silica-alumina.

SUMMARY OF THE INVENTION

The procedure according to the present invention permits obtaining high purity ethylene or a directly usable ethylene/carbon monoxide mixture, at the same time as it permits arriving at a high conversion of the ester and at a high selectivity and productivity.

Briefly, the present invention comprises a process for the manufacture of high purity ethylene comprising catalytic decomposition in the gaseous phase of ethyl esters of aliphatic carboxylic acids at a temperature between about 150° to 300° C., in the presence of a catalyst selected from among the zeolites whose pore diameter is at least about 0.6 nm.

DETAILED DESCRIPTION

While any zeolite having a pore diameter of at least about 0.6 nm can be used, preferably employed among such zeolites are mordenites, zeolites X, and zeolites Y.

The preparation of large-pore mordenites is described, for example, in U.S. Pat. No. 4,018,514 and in Mol. Sieves Pap. Conf., 1967, 78, Soc. Chem. Ind. London, by D. DOMINE and J. QUOBEX.

Zeolite X is described, for example, in U.S. Pat. No. 2,882,244 and zeolite Y in U.S. Pat. No. 3,130,007.

The zeolites suitable for the procedure of the invention can be in the basic form, in the partially or totally acidified form, or in the partially dealuminated form.

They can be used, for example, on the form of small spheres or cylinders of a diameter most often between 1 and 5 mm, obtained when the zeolite is manufactured in the state of a powder, by applying to the latter the classical procedures of agglomeration, extrusion, and pelleting into the shape desired.

The process of decomposition of the esters is carried out at a pressure just above the pressure sufficient in order to overcome the pressure drop across the catalytic bed.

Although the process can be conducted at temperatures outside the preferred range of about 150° to 300° C., a temperature lower than 150° C. will result in an ester decomposition rate that is too slow to remain compatible with, in particular, the industrial requirements of productivity, while a temperature higher than 300° C. on its part involves a lowering of the selectivity and a risk of fouling the catalyst.

The temperature range of about 150° C. to 300° C. thus defined is particularly well suited for the decomposition of the ethyl esters of formic, acetic, and propionic acid. Such esters, or mixtures, thereof are the preferred esters.

The ester to be decomposed is vaporized prior to its passage over the catalyst. It can be introduced alone into the catalysis reactor, but also in the form of a gaseous mixture with an inert gas such as, for example, nitrogen.

The reaction time with the catalyst can vary within wide limits taking into consideration particularly the nature of the catalyst and of the ester. It is most generally between 10 and 100 seconds with the optimum time for each particular catalyst and ester being easily determined by routine experimentation on test batches.

The following examples, given by way of indication but not limiting, illustrate the procedure of the invention. For each one of them, the pressure is the pressure just above pressure sufficient in order to overcome the pressure drop across the catalytic bed.

EXAMPLE 1

In a tubular reactor made of Pyrex glass, having an internal diameter of 30 mm and capable of being raised to a controlled temperature, there are arranged 30 ml of cylindrical pellets having a diameter and height of 5 mm, obtained by the mechanical agglomeration of a mordenite in powder form manufactured by the Societe Chimique de la Grande Paroisse under the reference name of ALITE 180.HZ.

A gaseous mixture of nitrogen and ethyl formate containing 70.7% of ester by volume is introduced into the reactor where the decomposition of the ethyl formate is carried out at a temperature of 250° C.

The conversion of ethyl formate is equal to 100%.

The selectivity in ethylene is more than 98%, less than 2% of the ethyl formate used being converted into ethane.

The ethylene is obtained as a mixture with the carbon monoxide formed with a selectivity of 100% from the ethyl formate.

EXAMPLE 2

In the apparatus setup of Example 1, ethyl propionate was decomposed by the passage therethrough over 30 ml of the catalyst of Example 1 at a temperature of 250° C., of 3.36 l/h of a gaseous mixture of $N_2$/ethyl propionate containing 61.3% by volume of ester.

20% of the ester is converted with selectivities in ethylene and propionic acid which are, in both cases, above 98%.

EXAMPLE 3

By operating at 150° C., with 30 ml of the catalyst and apparatus of Example 1 and 3.8 l/h of a mixture of $N_2$/ethyl acetate in the gaseous state containing 65.8% by volume of ester, the conversion of the latter into ethylene and acetic acid is equal to 5.5%, the selectivity in ethylene as well as in acetic acid being 100%.

EXAMPLE 4

By operating as in Example 3, but at 250° C. and without the introduction of nitrogen, the conversion of the ester amounts to 40%, the selectivity in acetic acid is 100%, and the purity of the ethylene collected is above 99.9%, only traces of methane having been detected.

EXAMPLE 5

30 ml of extrudates having a diameter of about 3.2 mm and composed of a mordenite commercially sold under the name of ZEOLON 900 Na by the NORTON COMPANY, are arranged in the reactor of Example 1.

3.67 l/h of a mixture of $N_2$/ethyl acetate in the gaseous state containing 64.6% of ester by volume are passed over the catalyst at 250° C.

The conversion of the ester amounts to 15%. The ethylene and the acetic acid are obtained with a selectivity of practically 100%, the ethylene obtained containing less than 0.2% of methane.

EXAMPLE 6

The catalyst of Example 5 is replaced by an equal volume of extrudates of the same dimension of mordenite ZEOLON 900H commercially sold by the NORTON COMPANY.

3.69 l/h of a gaseous mixture of $N_2$/ethyl acetate containing 66.7% ester by volume are passed over the catalyst at 300° C. in the reactor of Example 1.

During the course of the catalytic decomposition, 55% of the ester is converted, with the selectivity in acetic acid attaining 99% and the ethylene produced having a purity above 99.5%.

EXAMPLE 7

In the reactor of Example 1, 3.85 l/h of a gaseous mixture of nitrogen and ethyl acetate containing 66.3% of ester by volume are passed at 300° C. over 30 ml of zeolite 13X; in the form of spheres having a diameter of 1.4 mm to 2.4 mm, supplied by the Touzart and Matignon Company.

13% of the ester is converted, with a selectivity of 100%, into ethylene and acetic acid.

The ethylene produced contains only trace amounts of methane and hydrocarbons containing three carbon atoms.

EXAMPLE 8

The catalyst of Example 7 is subjected to washing with the help of an ammonium nitrate solution followed by a thermal treatment at 550° C.

30 ml of zeolite 13X thus partially acidified serve for the decomposition at 250° C. of the ethyl acetate contained at a concentration of 63.4% by volume in the 3.96 l/h of gaseous mixture of $N_2$/ester passing over the catalyst in the reactor of Example 1.

22% of the ester is selectively converted into ethylene and acetic acid, with the ethylene produced containing only traces of methane.

EXAMPLE 9

A gaseous mixture of $N_2$/ethyl acetate containing the ester at a concentration of 61.9% by volume are passed at a rate of 3.8 l/h, at a temperature of 180° C., over 30 ml of zeolite Y from the ALFA Company under the reference number of LZY 82 in the form of extrudates having a diameter of about 1.6 mm in the reactor of Example 1.

Under these conditions, 70% of the ester is converted into ethylene and acetic acid with a selectivity of practically 100%.

The ethylene collected in fact only contains traces of methane.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the manufacture of high purity ethylene by the catalytic decomposition in the gaseous phase of an ethyl ester of an aliphatic carboxylic acid comprising carrying out said decomposition at a temperature between about 150° to 300° C. in the presence of a zeolite having a pore diameter of at least 0.6 nm.

2. The process of claim 1 wherein the ester is selected from ethyl formate, ethyl acetate, ethyl propionate, or mixtures thereof.

3. The process of claim 1 wherein the zeolite is selected from a mordenite, a zeolite X, or a zeolite Y.

4. The process of claim 3 wherein the zeolite is in the basic form, or in partially or totally acidified form, or in partially dealuminated form.

5. The process of claim 4 wherein the zeolite is used in the form of small balls, extrudates, or pellets having a dimension of between about 1 and 5 mm.

6. The process of any one of claims 1 to 5 wherein the catalytic decomposition of the esters is carried out at the pressures just above that sufficient to overcome the pressure drop across the catalytic bed.

7. The process of any one of claims 1 to 5 wherein the catalytic decomposition time is between about 10 to 100 seconds.

* * * * *